US012653623B2

(12) United States Patent
Govari et al.

(10) Patent No.: US 12,653,623 B2
(45) Date of Patent: Jun. 16, 2026

(54) ELECTROPHYSIOLOGY MAPPING USING CATHETER SPLINES DEFLECTION MODELING

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 753 days.

(21) Appl. No.: 18/089,428

(22) Filed: Dec. 27, 2022

(65) Prior Publication Data

US 2024/0206978 A1 Jun. 27, 2024

(51) Int. Cl.
*A61B 34/20* (2016.01)
*A61B 18/14* (2006.01)
*A61B 5/06* (2006.01)

(52) U.S. Cl.
CPC .......... *A61B 34/20* (2016.02); *A61B 18/1492* (2013.01); *A61B 5/062* (2013.01)

(58) Field of Classification Search
CPC ............ A61B 34/20; A61B 2034/2046; A61B 2034/2048–2065; A61B 5/061; A61B 5/062; A61B 5/064–068; A61B 5/6858; A61B 5/6859; A61B 2018/0022; A61B 2018/00232; A61B 2018/00226–00261; A61B 5/6853
See application file for complete search history.

(56) References Cited

U.S. PATENT DOCUMENTS

| 5,443,489 A | 8/1995 | Ben-Haim |
|---|---|---|
| 5,539,199 A | 7/1996 | Ruckh et al. |
| 5,558,091 A | 9/1996 | Acker et al. |
| 5,899,860 A | 5/1999 | Pfeiffer et al. |
| 6,172,499 B1 | 1/2001 | Ashe |
| 6,239,724 B1 | 5/2001 | Doron et al. |
| 6,332,089 B1 | 12/2001 | Acker et al. |

(Continued)

OTHER PUBLICATIONS

U.S. Appl. No. 17/874,224, filed Jul. 26, 2022.

(Continued)

*Primary Examiner* — Linda C Dvorak
*Assistant Examiner* — Davina E. Lee
(74) *Attorney, Agent, or Firm* — Clayton, McKay & Bailey, PC

(57) ABSTRACT

A system includes an expandable distal-end assembly and a processor. The expandable distal-end assembly is coupled to a distal end of a shaft for insertion into a cavity of an organ of a patient, the assembly including one or more electrodes. The processor is configured to (i) receive location signals from each of a distal and proximal location of the distal-end assembly, (ii) receive location signals indicative of a relative orientational angle from one or more sensors that are located at the distal-end assembly and configured to output signals indicative of the change in the relative orientation, (iii) estimate angular position in the azimuthal plane of each of a plurality of splines extending from the proximal to distal end of the distal-end assembly, and (iv) estimate respective locations of one or more of the electrodes in three dimensional space based on the estimated angular position of each of the splines.

22 Claims, 3 Drawing Sheets

(56)  References Cited

U.S. PATENT DOCUMENTS

| | | | |
|---|---|---|---|
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,748,255 | B2 | 6/2004 | Fuimaono et al. |
| 6,788,967 | B2 | 9/2004 | Ben-Haim et al. |
| 6,839,588 | B1 | 1/2005 | Rudy |
| 6,892,091 | B1 | 5/2005 | Ben-Haim et al. |
| 7,536,218 | B2 | 5/2009 | Govari et al. |
| 7,596,406 | B2 | 9/2009 | Boese et al. |
| 7,756,576 | B2 | 7/2010 | Levin |
| 7,848,787 | B2 | 12/2010 | Osadchy |
| 7,869,865 | B2 | 1/2011 | Govari et al. |
| 8,456,182 | B2 | 6/2013 | Bar-Tal et al. |
| 9,204,929 | B2 | 12/2015 | Solis |
| 2003/0078494 | A1* | 4/2003 | Panescu ............. A61B 18/1492 |
| | | | 600/424 |
| 2013/0274582 | A1 | 10/2013 | Afonso |
| 2015/0223757 | A1* | 8/2015 | Werneth ............... A61B 5/0205 |
| | | | 600/301 |
| 2018/0014751 | A1 | 1/2018 | Hill |
| 2018/0184982 | A1* | 7/2018 | Basu .................... A61B 5/6858 |
| 2020/0138334 | A1 | 5/2020 | Hill |
| 2020/0138525 | A1 | 5/2020 | Hill |
| 2021/0059549 | A1* | 3/2021 | Urman ................... G06F 17/18 |
| 2021/0059608 | A1 | 3/2021 | Beeckler et al. |
| 2024/0197393 | A1* | 6/2024 | Kingston ............... A61B 5/367 |

OTHER PUBLICATIONS

Oesterlein, Tobias, Basket-Type Catheters: Diagnostic Pitfalls Caused by Deformation and Limited Coverage; BioMed Research International, Hindawi Publishing Company, vol. 2016; 13 pgs.; Dec. 13, 2016.

European Search Report for corresponding EPA No. 23219896.0 dated Jun. 4, 2024.

* cited by examiner

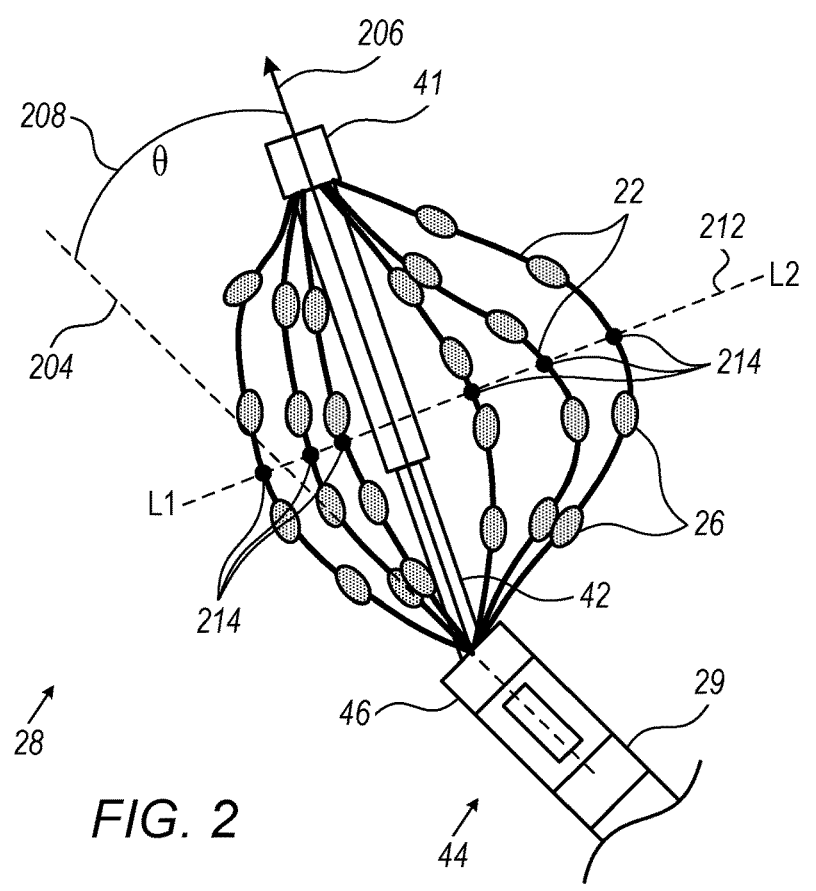
FIG. 2
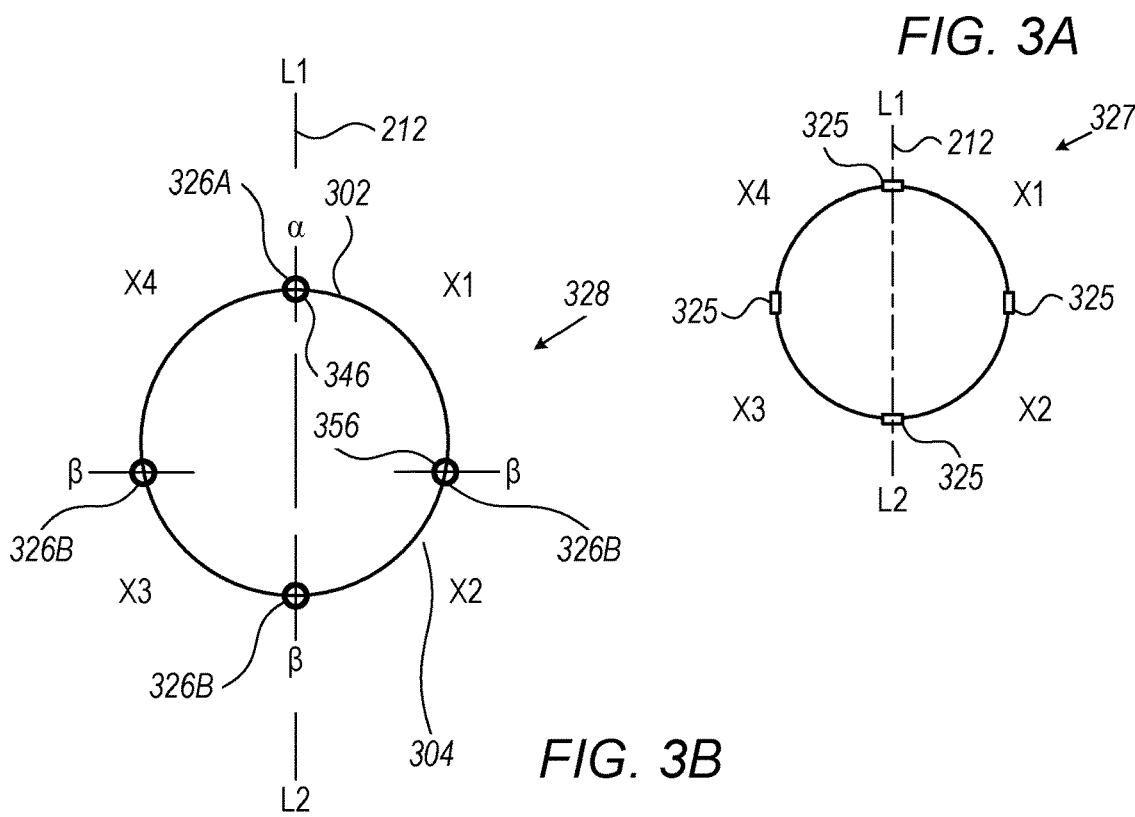
FIG. 3A
FIG. 3B

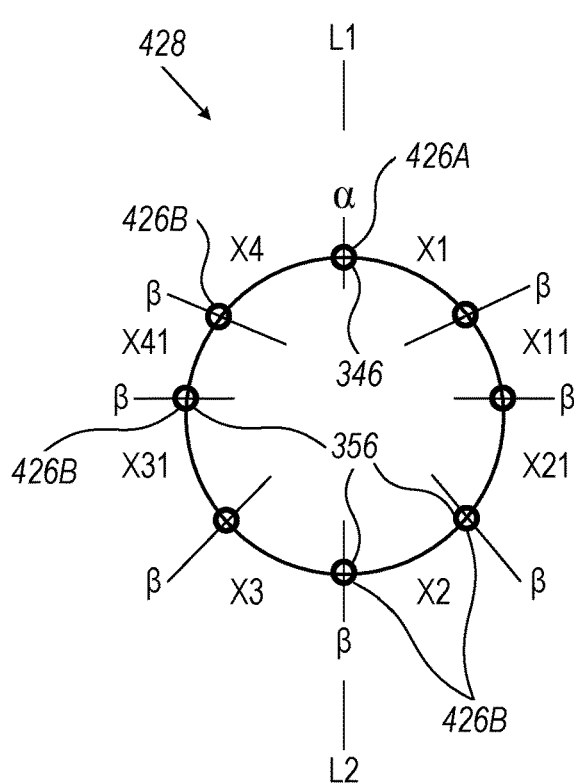
*FIG. 4*
*FIG. 5*
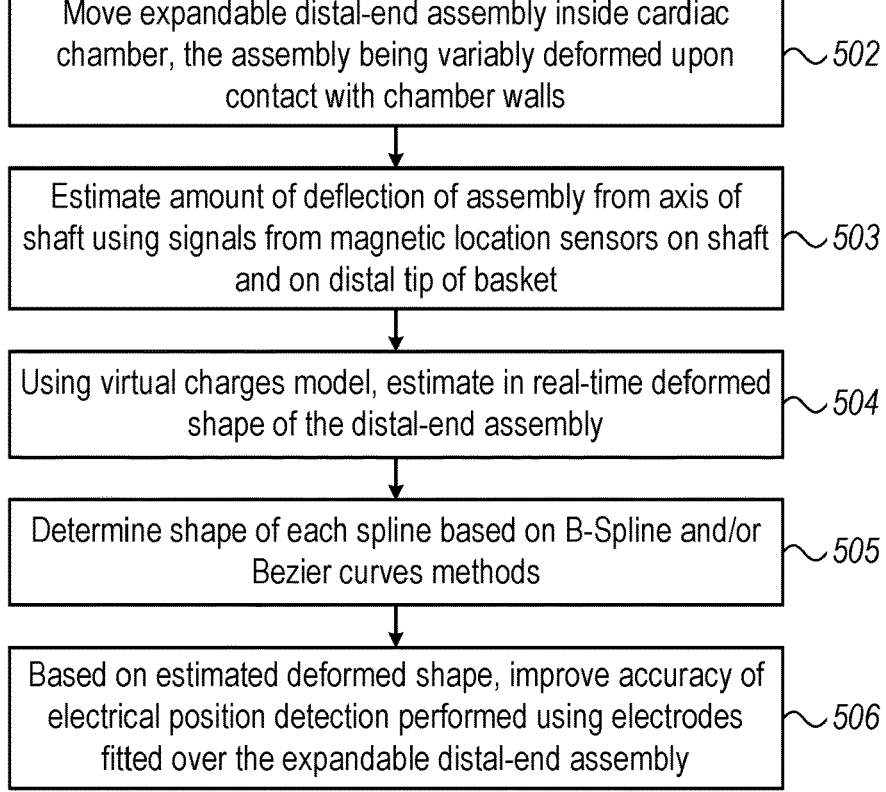

ELECTROPHYSIOLOGY MAPPING USING CATHETER SPLINES DEFLECTION MODELING

FIELD OF THE DISCLOSURE

The present disclosure relates generally to invasive medical probes, and particularly to cardiac catheters.

BACKGROUND OF THE DISCLOSURE

Basket catheters typically have an elongated catheter body and a basket-shaped electrode assembly mounted at the distal end of the catheter body. The assembly has proximal and distal ends and comprises a plurality of splines connected at their proximal and distal ends. Each spline comprises at least one electrode. The assembly may have an axial elongated expander which is longitudinally movable relative to the catheter by an electrophysiology (EP) professional to vary the configuration of the basket between an expanded arrangement wherein the splines bow radially outwardly and a collapsed arrangement wherein the splines are arranged generally along the axis of the catheter body.

The catheter may further comprise a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the splines of the assembly to find the positions of the at least one electrode of each spline as long as the longitudinal orientation of the basket is parallel to that of the shaft. A basket catheter that includes two location sensors for providing location information about each of the electrodes on the electrode assembly is described in U.S. Pat. No. 9,204,929.

The present disclosure will be more fully understood from the following detailed description of the examples thereof, taken together with the drawings, in which:

BRIEF DESCRIPTION OF THE DRAWINGS

FIG. 2 is a schematic, pictorial illustration of a basket catheter in a deformed shape when pressed against tissue, in accordance with an example of the present disclosure;

FIGS. 3A and 3B are schematic models of a frontal cross section of a basket assembly comprising four spline locations when the assembly is in neutral state and when pressed against tissue, respectively, in accordance with an example of the present disclosure;

FIG. 4 is a schematic model of a frontal cross section of a basket assembly comprising eight spline locations when the assembly is pressed against tissue, in accordance with examples of the present disclosure; and FIG. 5 is a flow chart that schematically illustrates a method to estimate a shape of a basket catheter pressed against tissue, in accordance with an example of the present disclosure.

DETAILED DESCRIPTION OF EXAMPLES

Overview

Figure 1:
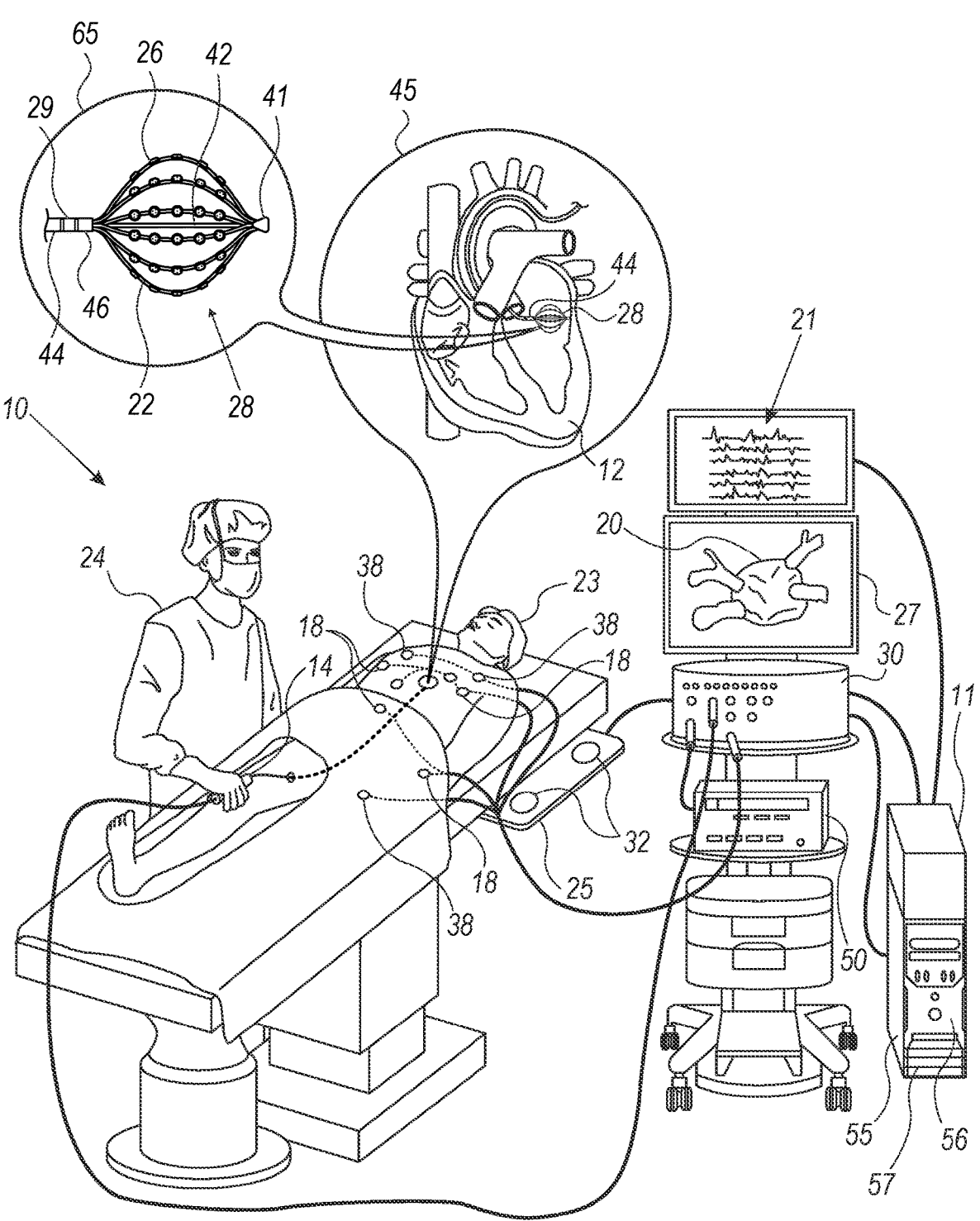
FIG. 1 is a schematic, pictorial illustration of a catheter-based electro-anatomical (EA) mapping and ablation system, in accordance with an example of the present disclosure.

A cavity of an organ of a patient, such as a cardiac cavity, can be mapped using a catheter having multiple electrodes fitted at an expandable distal-end assembly of the catheter. In a mapping procedure, a physician first inserts the expandable distal-end assembly, e.g., of a basket catheter (which is coupled to a distal end of a shaft) into the cavity. Then the physician expands the assembly and manually moves the expanded distal-end assembly in order to contact chamber walls.

Using location signals generated by one or more magnetic based location sensors mounted at defined position on the catheter, a processor may calculate the respective locations of the sensors inside the cardiac cavity. Using sensor locations and a known shape of the distal-end assembly, the processor may calculate locations of the multiple electrodes.

In addition, an approximate location of each of the electrodes may also be determined based on an impedance-based tracking method (e.g., ACL by Biosense Webster). In impedance-based tracking, electrical current is directed toward the multiple electrodes of the catheter and sensed at electrode skin patches so that the location of each catheter electrode can be triangulated via the electrode patches.

Using the calculated electrode locations and the respective EP signals, the processor can derive an electroanatomical (EA) map of the cardiac cavity surface. In some examples, such an EA map, may indicate graphically potential arrhythmogenic locations over the cavity wall tissue that should be ablated for treatment of arrhythmia.

In the description below, for example, a basket catheter that carries multiple electrodes on its splines acquires locations and respective EP values, together called hereinafter "data points," that a processor may use for generating the aforementioned EA map of the cardiac chamber.

As noted above, the calculation of the locations of the sensors may assume a certain geometry of the expanded distal-end assembly, and in particular the relative three-dimensional (3D) geometrical relationship among the electrodes. In some examples, the curvature of each spline is determined with a $4^{th}$ order b-spline curve and/or a Bezier curve. An example system and method for tracking coordinates of electrodes with Bezier curves is described in U.S. Ser. No. 17/874,224 filed on Jul. 26, 2022. The $4^{th}$ order b-spline curve needs four constraints. Two constrains are the end points (This is determined from the magnetic position sensors on the shaft and on the distal end of the basket). An additional constraint is the assumed zero slope of the spline at the proximal end (this is an assumption made). Final constraint is the known length of the spline.

Once the processor determined the curvature of each spline, a next step is to know the angular position of each spline on the azimuthal plane. In a neutral state this is relatively simple as the splines are distributed evenly.

However, as a result of the physical contact with a cavity wall the shape of the expandable distal-end assembly inside the cavity may deform and thus deviate from the assumed shape. Therefore, when a basket shape is not well known due to variable deformations during EA mapping, measurement results relying on a known shape may produce distorted results.

For example, estimated locations of electrodes that are fitted on a plurality of expandable splines of the basket may differ from the actual locations, which may cause the processor to produce a distorted EA map of the cavity. To prevent this distortion, the processor needs to reconstruct the shape of the expandable distal-end assembly including multiple splines as the it deflects from the axis of the shaft.

In particular, when a basket type of an expandable distal-end assembly of a catheter bends due to a lateral force, e.g., when the basket is pressed against a wall of a chamber, the shape of the basket changes. In some examples, the distribution of the splines in the azimuthal plane shift as the basket deflects with respect to the axis of the shaft, e.g., when pressed against a wall. For example, the splines that face the wall (i.e., those opposite the direction of the bending) bunch together, while the splines that are in blood pool (i.e., away from the wall, in the direction of the bending) spread apart. The relative shift of the splines may occur to due to the resistance of the splines to torsional deformation. Optionally, the splines are formed as flat ribbons that resist torsional deformation. The change in basket shape affects an ability to estimate the location of multiple sensing electrodes that are fitted over the splines in 3D space. For example, a best fit of location signals from respective electrodes to a known distribution of the electrodes in space due to known mechanical shape of the basket is very inaccurate when the basket is pressed against wall tissue.

Examples of the present disclosure that are described herein provide a technique in which a processor models the varying shape of an expandable distal-end assembly of a catheter inside a cardiac chamber in real time, thereby improving accuracy of the electroanatomical mapping. For example, in some examples the processor runs a program to estimate, in real time, the deformed shape of the basket catheter as it is brought into contact with cavity walls inside a cardiac chamber. Using the deformed shape, the processor greatly improves the location accuracy of the aforementioned data points acquired during mapping resulting in the aforementioned more accurate EP maps.

As indicated above, when the basket is deflected, the splines lose the even distribution. This happens because the splines are formed as flat ribbons that resist torsional deformation. When assembly is deflected the splines bunch toward the equator (i.e., largest circumference of an azimuthal plane of the assembly) at opposite direction of the deflection and then separate above it.

The disclosed technique accounts for the uneven distribution by assuming that the splines repel each other by the amount of deflection. The processor applies a model for the repelling splines by placing a virtual charge in the middle of each spline. Based on the shape of each spline as modeled with the $4^{th}$ order b-spline curve and the angular position as modeled with the virtual charge we can define the shape and position of the splines and also determine location of the electrodes in the coordinate system of the EA map.

In some examples, the processor models the change in shape using a model analogous to forces exerted by "virtual electrical charges. In the disclosed mechanical model, for example, position of a given spline of a basket type distal-end assembly in the azimuthal plane is related to angle of deflection and proximity to a spline with the smallest angle of deflection, e.g. a spline that is pressed against the tissue.

In the model, the processor assigns (e.g., positions at a spline location of contact) one virtual charge, a, to represent the elastic potential caused by the encountered expandable distal-end assembly being deflected, e.g., deflected as it is pressed against wall tissue. Another virtual charge, β, is positioned at the relative location of each of the other splines. In free space, the expandable distal-end assembly is unaffected by external forces, so all virtual charges are equal to B. In such a case the splines are dispersed evenly.

When pressed against a tissue wall, the expandable distal-end assembly bends relative to the shaft with an angle ⊖, as seen in FIG. 2 below. The bending angle is estimated, for example from magnetic position sensors fitted at proximal and distal ends of the assembly. As another example, the bending angle ⊖ is estimated from location signals from multiple electrodes on the splines.

In some example embodiments, deformation of a balloon catheter is modeled based on defining virtual splines on the balloon catheter. A virtual spline may extend along a surface of a balloon catheter from a distal tip of the balloon to the proximal end of the balloon connected to the shaft. In some examples, the angular positioning of the virtual splines defines warping of a balloon surface that may occur due to deflection of the balloon. The warped surface of the balloon may alter position of the electrodes mounted on the balloon surface.

The disclosed model assigns a virtual charge α to the pressed spline based on the detected bending angle. Optionally and preferably, a spline that is most proximal to a longitudinal axis of the shaft is selected as the spline with virtual charge α. The bending angle ⊖ defines α based on the following equation:

$$\alpha(\theta) = \beta(1 + K\theta)$$

Here K is a coefficient of elastic stiffness that represents the stiffness of the splines, and α(⊖)>β for ⊖>0. If α is large enough, compared with β, (i.e., has significant bending), the splines are dispersed unevenly, as can be seen in a cross section (e.g., an equatorial plane, or a tilted plane) of the assembly in FIG. 3. The analysis is performed within the Azimuthal plane of the basket assembly.

Using elastic equations analog of equations between electrical charges, the model determines the uneven distances between any number of splines. The splines may be actual splines or may be virtual splines that define a balloon shape of the basket catheter. #

Using the estimated deformed shape, the processor can better estimate the true locations of the electrodes, and therefore improve accuracy of electrical position detection performed using electrodes fitted over the expandable distal-end assembly.

SYSTEM DESCRIPTION

FIG. 1 is a schematic, pictorial illustration of a catheter-based electroanatomical (EA) mapping and ablation system 10, in accordance with an example of the present disclosure.

System 10 includes one or more catheters, which are percutaneously inserted by physician 24 through the patient's vascular system into a chamber or vascular structure of a heart 12. Typically, a delivery sheath catheter is inserted into the left or right atrium near a desired location in heart 12. Thereafter, one or more catheters in turn can be inserted into the delivery sheath catheter so as to arrive at the desired location. The one or more catheters may include catheters dedicated for sensing intracardiac electrogram (IEGM) signals, catheters dedicated for ablating and/or catheters dedicated for both sensing and ablating. An example basket catheter 14 that is configured for sensing IEGM is illustrated herein. As seen in inset 45, physician 24 brings a basket assembly 28 (also called hereinafter "expandable distal-end assembly 28") fitted on a shaft 44 of catheter 14 into contact with the heart wall for sensing a target site in heart 12. For ablation, physician 24 similarly brings a distal end of an ablation catheter to a target site for ablating.

As seen in inset 65, basket catheter 14 is an exemplary catheter that includes one and preferably multiple electrodes 26 optionally distributed over a plurality of splines 22 at expandable distal-end assembly 28 and configured to sense IEGM signals. Catheter 14 additionally includes (i) a proximal position sensor 29 embedded in or near basket assembly 28 to track the position of a distal end 46 of shaft 44, and (ii) a distal position sensor 41 for a tracking position of the distal end of basket assembly 28. Optionally and preferably, position sensors 29 and 41 are magnetic-based position sensors including magnetic coils for sensing three-dimensional (3D) position.

Magnetic-based position sensors 29 and 41 may be operated together with a location pad 25 including a plurality of magnetic coils 32 configured to generate magnetic fields in a predefined working volume. Real-time orientation of basket assembly 28 of catheter 14 relative to distal end 46 of shaft 44 is calculated from tracked locations of sensors 29 and 41 (locations being tracked using magnetic fields generated with location pad 25 and sensed by magnetic-based position sensors 29 and 41). This relative orientation is manifested by an angle formed between distal end 46 and an expansion rod 42 of expandable assembly 28, as described in FIG. 2.

Details of the magnetic-based position sensing technology are described in U.S. Pat. Nos. 5,539,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish a location reference for location pad 25 as well as impedance-based tracking of electrodes 26. For impedance-based tracking, electrical current is directed toward electrodes 26 and sensed at electrode skin patches 38 so that the location of each electrode can be triangulated via electrode patches 38. Details of the impedance-based location tracking technology are described in U.S. Pat. Nos. 7,536,218; 7,756,576; 7,848,787; 7,869,865; and 8,456,182.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses that may be used to effect irreversible electroporation (IRE), or combinations thereof.

Patient interface unit (PIU) 30 is configured to establish electrical communication between catheters, electrophysiological equipment, power supply and a workstation 55 for controlling operation of system 10. Electrophysiological equipment of system 10 may include, for example, multiple catheters, location pad 25, body surface ECG electrodes 18, electrode patches 38, ablation energy generator 50, and recorder 11. Optionally and preferably, PIU 30 additionally includes processing capability for implementing real-time computations of catheter locations and for performing ECG calculations.

Workstation 55 includes memory 57, processor unit 56 with memory or storage with appropriate operating software loaded therein, and user interface capability. Workstation 55 may provide multiple functions, optionally including (1) modeling endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Catheter Spline Deflection Models

FIG. 2 is a schematic, pictorial illustration of a basket catheter with a deformed shape when pressed against tissue, in accordance with an example of the present disclosure. FIG. 2 shows the impact of the pressing force on the shape of the basket's expandable distal-end assembly 28. As seen, the elongation rod 42 of assembly 28 develops an angle $\ominus$ 208 with respect to the distal end 46 of shaft 44. Angle 208 is defined between a longitudinal axis 206 of elongation rod 42 and a longitudinal axis 208 of distal end 46. Using position sensors 29 and 41, and known geometry of elongation rod 42 and of distal end 46, the processor can readily calculate angle $\ominus$ 208.

Unknown, however, is the shape followed by splines 22, though it is evident that splines 22 on the pressed side (L1) are compressed inwards, whereas splines 22 on the free side (e.g., in a cardiac chamber blood pool) bow outwards. The analysis of the deformed shape is done in FIGS. 3 and 4 by looking at a frontal cross-sectional plane L1-L2 212 (e.g., the azimuthal plane). Since splines 22 are elastic and continuous, the processor can reconstruct the entire basket shape by finding spline locations 214 in one such plane.

FIGS. 3A and 3B are schematic models 327 and 328 of frontal a cross section of a basket assembly comprising four spline locations 325 and 326 when the assembly is in neutral state (3A) and when pressed against tissue (3B), respectively, in accordance with an example of the present disclosure.

Following the definitions of FIG. 2, the cross-section is along azimuthal plane L1-L2.

There are four unknowns: the inter-spline distances X1, X2, X3 and X4. As seen in FIG. 3A, in a neutral state of basket distal end, e.g., with no lateral force applied, for a total circumference of the basket, $2\ell$, X1=X2=X3=X4= $\ell/2$.

As seen in FIG. 3B (and FIG. 2), the angular positions of the splines shift when pressed against tissue. For example, splines 326B are bunched together and distanced from electrode 326. To model the angular position of each spline on the azimuthal plane, virtual charges $\alpha$ (346) and $\ominus$ (356) are placed at the respective intersection points 326A and 326B of the splines within plane L1-L2.

Because of symmetry considerations X3=X2 and X4=X1, there are two unknowns.

At a given expanded state the total circumference of the basket, $2\ell$ is a constant of the expandable frame, which gives one equation:

$$X1 + X2 = \ell$$

A second equation of an equilibrium is derived from elastic potentials:

$$\frac{\alpha\beta}{X1} = \frac{\beta^2}{X2}$$

This gives the solution, $$X1 = \frac{\alpha}{\alpha+\beta} \cdot \ell \text{ and } X2 = \frac{\beta}{\alpha+\beta} \cdot \ell.$$

For an example case where $\alpha=2\beta$, the displacement of an electrode at the azimuthal plane can amount to several millimeters.

FIG. 4 is a schematic model 428 of a frontal cross section of a basket assembly comprising eight spline locations when the assembly is pressed against tissue, in accordance with examples of the present disclosure. Following the definitions of FIG. 2, the cross-section is along plane L1-L2.

As seen, virtual charges $\alpha$ (346) and $\beta$ (356) are placed at the respective intersection points 426A and 426B of the splines within plane L1-L2.

There are eight unknowns: the inter-spline distances X1, X11, X21, X2, X3, X31, X41 and X4. In a neutral state of the basket, for a total circumference of the basket, $2\ell$, X1=X11=X21=X2=X3=X31=x41=x4= $\ell$/4. Symmetry considerations lead to X3=X2, X31=X21, X41=X11, and X4=X1, so there are four unknowns.

At a given expanded state the total circumference of the basket $2\ell$ is a constant of the expandable frame, which gives one equation:

$$X1 + X11 + X21 + X2 = \ell$$

A second equation is of an equilibrium derived from the elastic potentials:

$$\frac{\alpha\beta}{X1} = \frac{\beta^2}{X11} + \frac{\beta^2}{X21} - \frac{\beta^2}{X2}$$

assuming, X2$\cong$X1 and X21$\cong$X11.

This gives the solution, $$X11 \approx \frac{\beta}{\alpha+3\beta} \cdot \ell \text{ and } X2 \approx \frac{\alpha+\beta}{2(\alpha+3\beta)} \cdot \ell.$$

A Method for Estimating a Shape of a Basket Catheter Pressed Against Tissue

FIG. 5 is a flow chart that schematically illustrates a method to estimate a shape of a basket catheter pressed against tissue, in accordance with an example of the present disclosure. The algorithm, according to the presented example, carries out a process that begins with physician 24 moving expandable distal-end assembly 28 inside a cardiac chamber, leading to assembly 28 being variably deformed, as seen in FIG. 2, upon contact with the chamber walls, at a catheter acquisition step 502.

Assembly 28 carries multiple electrodes on its splines to acquire locations and respective EP values, ("data points") that a processor may use for generating the aforementioned EA map of the cardiac chamber. When, for example, the basket shape is not well known as it variably deforms during EA mapping, measurement results relying only one the location as sensed by the magnetic location sensors may produce distorted results. For example, assumed locations of electrodes that are fitted on a plurality of expandable splines of the basket may be wrong, which may cause the processor to produce a distorted EP map of the cavity.

At a deflection estimation step 503, the processor estimates an amount of deflection (i.e., bend angle $\theta$ and $\phi$ in roll and pitch directions) from the longitudinal axis of the shaft using signals from magnetic location sensors located one on the shaft and the other on the distal tip of the basket.

To correct (e.g., apply a best fit to) the electrode locations, the processor uses the measured bend angles $\theta$ and $\phi$ together with the aforementioned mechanical model of the assembly shape, that is based on virtual charges $\alpha(\theta, \phi)$ (346) and $\ominus$ (356). By solving the model in real time, the processor estimates the angular position on the azimuthal plane of each spline, at a distal-end assembly shape estimation step 504.

At a spline shape determination step 505, the processor determines the shape of each spline based on B-Spline and/or Bezier curves methods.

Finally, based on the estimated deformed shape and angular positioning, the processor determines 3D position of one or more electrodes on the basket. The 3D position determined improves the accuracy of data points acquired using electrical detection (e.g., aforementioned impedance-based location tracking), by the locations conforming with the deformed shape at any given time, at location tracking improving step 506.

The flow chart shown in FIG. 5 is chosen purely for the sake of conceptual clarity. The present example may also comprise additional steps of the algorithm, such as estimating contact force. This and other possible steps are omitted from the disclosure herein purposely in order to provide a more simplified flow chart.

EXAMPLES

Example 1

A system (10) includes an expandable distal-end assembly (28) and a processor (56). The expandable distal-end assembly is coupled to a distal end of a shaft (44) for insertion into a cavity of an organ of a patient, the assembly including one or more electrodes (26). The processor is configured to (i) receive location signals from each of a distal and proximal location of the distal-end assembly, (ii) receive location signals indicative of a relative orientational angle (208) from one or more sensors (41, 46) that are located at the distal-end assembly (28) and configured to output signals indicative of the change in the relative orientation, (iii) estimate angular position in the azimuthal plane (212) of each of a plurality of splines (22) extending from the proximal to distal end of the distal-end assembly (28), and (iv) estimate respective locations of one or more of the electrodes (26) in three dimensional space based on the estimated angular position of each of the splines (22).

Example 2

The system (10) according to example 1, wherein the splines are virtual splines along a surface of a balloon catheter.

Example 3

The system (10) according to any of examples 1 and 2, wherein the splines (22) are shaped as flat ribbons.

Example 4

The system (10) according to any of examples 1 through 3, wherein the distal-end assembly (28) comprises multiple splines (22) having the electrodes (26) disposed thereon, and wherein the processor (56) is configured to estimate the angular position in the azimuthal plane (212) of each of a plurality of splines (22) depending on elastic coefficients of the splines.

Example 5

The system (10) according to any of examples 1 through 3, wherein the one or more sensors (41, 46) comprise a first magnetic position sensor (46) located at a proximal end of the distal-end assembly (28) and a second magnetic position sensor (41) located at a distal end of the distal-end assembly (28).

Example 6

The system (10) according to any of examples 1 through 3, wherein the one or more sensors comprise a force sensor located at a proximal end of the distal-end assembly (28) and configured to output a signal indicative of the angle (212).

Example 7

The system (10) according to any of examples 1 through 6, wherein, in a neutral position, a first and second longitudinal axes (204, 206) of a catheter are (14) parallel to one another.

Example 8

The system (10) according to any of examples 1 through 7, wherein the distal-end assembly (28) comprises multiple splines (22), and wherein the processor (56) is configured to estimate the angular position in the azimuthal plane (212) of each of a plurality of splines by estimating respective shapes of the splines (22) based on b-spline or Bezier curve.

Example 9

The system (10) according to any of examples 1 through 8, wherein the processor (56) is configured to estimate the angular position in the azimuthal plane (212) of each of a plurality of splines (22) by using a mechanical model in which an angular position of a given spline in the azimuthal plane is related to (i) a distance between the given spline and a spline that is most proximal to a longitudinal axis of the shaft, and (ii) a virtual charge (346, 356) assigned to each spline.

Example 10

The system (10) according to claim any of examples 1 through 9, wherein the processor (56) is further configured to, using the estimated angular position in the azimuthal plane of each of a plurality of splines (22), improve accuracy of electrical position detection performed by electrodes (26) fitted over the expandable distal-end assembly (28).

Example 11

The system (10) according to any of examples 1 through 10, wherein the cavity is a cardiac cavity.

Example 12

A method includes inserting into a cavity of an organ of a patient an expandable distal-end assembly (28) coupled to a distal end of a shaft (44), the expandable distal-end assembly (38) comprising one or more electrodes (26). Location signals are received from each of a distal and proximal location of the distal-end assembly (28). Location signals indicative of a relative orientational angle are received from one or more sensors (41, 46) that are located at the distal-end assembly and configured to output signals indicative of the change (208) in the relative orientation. Angular position is estimated in the azimuthal plane of each of a plurality of splines (22) extending from the proximal to distal end of the distal-end assembly (28). Respective locations are estimated of one or more of the electrodes in three-dimensional space based on the estimated angular position of each of the splines. #

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A system, comprising:
an expandable distal-end assembly coupled to a distal end of a shaft for insertion into a cavity of an organ of a patient, the expandable distal-end assembly comprising one or more electrodes; and
a processor, which is configured to:
receive location signals from each of a distal and proximal location of the distal-end assembly;
receive location signals indicative of a relative orientational angle from one or more sensors that are located at the distal-end assembly and configured to output signals indicative of a change in the relative orientational angle;
estimate angular position in the azimuthal plane of each of a plurality of splines extending from the proximal to distal end of the distal-end assembly; and
estimate respective locations of the one or more electrodes in three dimensional space based on the estimated angular position of each of the splines.

2. The system according to claim 1, wherein the splines are virtual splines along a surface of a balloon catheter.

3. The system according to claim 1, wherein the splines are shaped as flat ribbons.

4. The system according to claim 1, wherein the distal-end assembly comprises multiple splines having the electrodes disposed thereon, and wherein the processor is configured to estimate the angular position in the azimuthal plane of each of the plurality of splines depending on elastic coefficients of the splines.

5. The system according to claim 4, wherein the one or more sensors comprise a first magnetic position sensor located at the proximal end of the distal-end assembly and a second magnetic position sensor located at the distal end of the distal-end assembly.

6. The system according to claim 4, wherein the one or more sensors comprise a force sensor located at the proximal end of the distal-end assembly and configured to output a signal indicative of the relative orientational angle.

7. The system according to claim 1, wherein, in a neutral position, a first and second longitudinal axes of a catheter are parallel to one another.

8. The system according to claim 1, wherein the distal-end assembly comprises multiple splines, and wherein the processor is configured to estimate the angular position in the azimuthal plane of each of the plurality of splines by estimating respective shapes of the splines based on b-spline or Bezier curve.

9. The system according to claim 1, wherein the processor is configured to estimate the angular position in the azimuthal plane of each of the plurality of splines by using a mechanical model in which an angular position of a given spline in the azimuthal plane is related to (i) a distance between the given spline and a spline that is radially closest to a longitudinal axis of the shaft, and (ii) a virtual charge assigned to each spline.

10. The system according to claim 1, wherein the processor is further configured to, using the estimated angular position in the azimuthal plane of each of the plurality of splines, improve accuracy of electrical position detection performed by the one or more electrodes fitted over the expandable distal-end assembly.

11. The system according to claim 1, wherein the cavity is a cardiac cavity.

12. A method, comprising:

inserting into a cavity of an organ of a patient an expandable distal-end assembly coupled to a distal end of a shaft, the expandable distal-end assembly comprising one or more electrodes;

receiving location signals from each of a distal and proximal location of the distal-end assembly;

receiving location signals indicative of a relative orientational angle from one or more sensors that are located at the distal-end assembly and configured to output signals indicative of a change in the relative orientational angle;

estimating angular position in the azimuthal plane of each of a plurality of splines extending from the proximal to distal end of the distal-end assembly; and estimating respective locations of the one or more electrodes in three-dimensional space based on the estimated angular position of each of the splines.

13. The method according to claim 12, wherein the splines are virtual splines along a surface of a balloon catheter.

14. The method according to claim 12, wherein the splines are shaped as flat ribbons.

15. The method according to claim 12, wherein the distal-end assembly comprises multiple splines having the electrodes disposed thereon, and comprising estimating the angular position in the azimuthal plane of each of the plurality of splines depending on elastic coefficients of the splines.

16. The method according to claim 15, wherein the one or more sensors comprise a first magnetic position sensor located at the proximal end of the distal-end assembly and a second magnetic position sensor located at the distal end of the distal-end assembly.

17. The method according to claim 15, wherein the one or more sensors comprise a force sensor located at the proximal end of the distal-end assembly and configured to output a signal indicative of the relative orientational angle.

18. The method according to claim 12, wherein, in a neutral position, a first and second longitudinal axes of a catheter are parallel to one another.

19. The method according to claim 12, wherein the distal-end assembly comprises multiple splines, and comprising estimating the angular position in the azimuthal plane of each of the plurality of splines by estimating respective shapes of the splines based on b-spline or Bezier curve.

20. The method according to claim 12, and comprising estimating the angular position in the azimuthal plane of each of the plurality of splines by using a mechanical model in which an angular position of a given spline in the azimuthal plane is related to (i) a distance between the given spline and a spline that is radially closest to a longitudinal axis of the shaft, and (ii) a virtual charge assigned to each spline.

21. The method according to claim 12, and comprising, using the estimated angular position in the azimuthal plane of each of the plurality of splines, improving accuracy of electrical position detection performed by the one or more electrodes fitted over the expandable distal-end assembly.

22. The method according to claim 12, wherein the cavity is a cardiac cavity.

* * * * *